(12) United States Patent
Donlon et al.

(10) Patent No.: US 8,590,534 B2
(45) Date of Patent: Nov. 26, 2013

(54) CUFF FOR USE WITH MEDICAL TUBING AND METHOD AND APPARATUS FOR MAKING THE SAME

(75) Inventors: Kieran Donlon, Ballymahon (IE); Jim Stephenson, Ballinasloe (IE)

(73) Assignee: Covidien LP, Mansfield, MA (US)

( * ) Notice: Subject to any disclaimer, the term of this patent is extended or adjusted under 35 U.S.C. 154(b) by 805 days.

(21) Appl. No.: 12/488,932

(22) Filed: Jun. 22, 2009

(65) Prior Publication Data

US 2010/0323048 A1 Dec. 23, 2010

(51) Int. Cl.
*A61M 16/00* (2006.01)

(52) U.S. Cl.
USPC ............ 128/207.15; 128/200.24; 128/200.26; 128/207.14

(58) Field of Classification Search
USPC ............ 128/200.24, 200.26, 205.19, 207.14; 606/108, 159, 191–198; 604/101, 604/101.01, 101.02, 101.05, 103.04, 604/103.05, 104, 96.01, 107, 523, 532, 536, 604/912, 915, 919
See application file for complete search history.

(56) References Cited

U.S. PATENT DOCUMENTS

| | | | |
|---|---|---|---|
| 2,927,584 A | 3/1960 | Wallace | |
| 3,625,793 A | 12/1971 | Sheridan et al. | |
| 3,627,282 A | 12/1971 | Kinslow, Jr. | |
| 3,769,983 A | 11/1973 | Merav | |
| 3,810,474 A | 5/1974 | Cross | |
| 3,822,238 A | 7/1974 | Blair et al. | |
| 3,901,246 A | 8/1975 | Wallace | |
| 3,913,565 A | 10/1975 | Kawahara | |
| 3,971,385 A | 7/1976 | Corbett | |
| 3,975,350 A | 8/1976 | Hudgin et al. | |
| 3,995,643 A | 12/1976 | Merav | |
| 4,022,217 A | 5/1977 | Rowean | |
| 4,096,223 A * | 6/1978 | Krall ............................ | 264/533 |
| 4,130,617 A | 12/1978 | Wallace | |
| 4,230,108 A | 10/1980 | Young | |
| 4,231,365 A | 11/1980 | Scarberry | |
| 4,235,239 A | 11/1980 | Elam | |
| 4,328,056 A * | 5/1982 | Snooks ........................ | 156/242 |
| 4,340,046 A | 7/1982 | Cox | |
| 4,357,288 A * | 11/1982 | Oas et al. ..................... | 264/40.6 |
| 4,417,576 A | 11/1983 | Baran | |
| 4,423,725 A * | 1/1984 | Baran et al. .............. | 128/207.15 |

(Continued)

FOREIGN PATENT DOCUMENTS

| | | |
|---|---|---|
| CA | 2353007 | 6/2000 |
| CN | 2208421 Y | 9/1995 |

(Continued)

OTHER PUBLICATIONS

International Search Report and Written Opinion for PCT Application No. PCT/US2010/03877 dated Sep. 4, 2011; 17 pgs.

(Continued)

*Primary Examiner* — Annette Dixon
(74) *Attorney, Agent, or Firm* — Fletcher Yoder PC

(57) ABSTRACT

A method of manufacturing more than one inflatable cuff per blow molding operation is provided. The method includes using two or more molds arranged in series and/or in parallel to simultaneously form two or more cuffs. The two or more cuffs may then be used in the manufacture of two or more respective endotracheal tubes. Apparatuses and systems for simultaneously forming the two or more cuffs are also provided.

23 Claims, 10 Drawing Sheets

(56) References Cited

U.S. PATENT DOCUMENTS

| | | |
|---|---|---|
| 4,456,000 A | 6/1984 | Schjeldahl et al. |
| 4,569,344 A | 2/1986 | Palmer |
| 4,638,539 A | 1/1987 | Palmer |
| 4,649,913 A | 3/1987 | Watson |
| 4,696,296 A | 9/1987 | Palmer |
| 4,700,700 A | 10/1987 | Eliachar |
| 4,791,920 A | 12/1988 | Fauza |
| 4,825,859 A | 5/1989 | Lambert |
| 4,825,861 A | 5/1989 | Koss |
| 4,834,726 A | 5/1989 | Lambert |
| 4,836,199 A | 6/1989 | Palmer |
| 4,838,255 A | 6/1989 | Lambert |
| 4,850,348 A | 7/1989 | Pell et al. |
| 4,867,153 A | 9/1989 | Lorenzen et al. |
| 4,872,579 A | 10/1989 | Palmer |
| 4,886,059 A | 12/1989 | Weber |
| 4,913,642 A | 4/1990 | Weber |
| 4,927,412 A | 5/1990 | Menasche |
| 4,938,741 A | 7/1990 | Lambert |
| 4,963,313 A | 10/1990 | Noddin et al. |
| 4,967,743 A | 11/1990 | Lambert |
| 4,979,505 A | 12/1990 | Cox |
| 5,020,534 A | 6/1991 | Pell et al. |
| 5,021,045 A | 6/1991 | Buckberg et al. |
| 5,025,806 A | 6/1991 | Palmer et al. |
| 5,029,580 A | 7/1991 | Radford et al. |
| 5,033,466 A | 7/1991 | Weymuller, Jr. |
| 5,060,646 A | 10/1991 | Page |
| 5,065,754 A | 11/1991 | Jensen |
| 5,074,840 A | 12/1991 | Yoon |
| 5,076,268 A | 12/1991 | Weber |
| 5,098,379 A | 3/1992 | Conway et al. |
| 5,103,816 A | 4/1992 | Krischbaum et al. |
| 5,107,829 A | 4/1992 | Lambert |
| 5,120,322 A | 6/1992 | Davis et al. |
| 5,122,122 A | 6/1992 | Allgood |
| 5,133,345 A | 7/1992 | Lambert |
| 5,135,516 A | 8/1992 | Sahatjian et al. |
| 5,137,671 A | 8/1992 | Conway et al. |
| 5,158,569 A | 10/1992 | Strickland et al. |
| 5,165,420 A | 11/1992 | Strickland |
| 5,176,638 A | 1/1993 | Don Michael |
| 5,190,810 A | 3/1993 | Kirschbaum et al. |
| 5,199,427 A | 4/1993 | Strickland |
| 5,201,310 A | 4/1993 | Turnbull et al. |
| 5,207,643 A | 5/1993 | Davis |
| 5,215,522 A | 6/1993 | Page et al. |
| 5,218,957 A | 6/1993 | Strickland |
| 5,230,332 A | 7/1993 | Strickland |
| 5,233,979 A | 8/1993 | Strickland |
| 5,246,012 A | 9/1993 | Strickland |
| 5,250,070 A | 10/1993 | Parodi |
| 5,251,619 A | 10/1993 | Lee |
| 5,261,896 A | 11/1993 | Conway et al. |
| 5,263,478 A | 11/1993 | Davis |
| 5,269,770 A | 12/1993 | Conway et al. |
| 5,277,177 A | 1/1994 | Page et al. |
| 5,290,585 A | 3/1994 | Elton |
| 5,304,121 A | 4/1994 | Sahatjian |
| 5,305,740 A | 4/1994 | Kolobow |
| 5,331,027 A | 7/1994 | Whitbourne |
| 5,337,745 A | 8/1994 | Benaron |
| 5,360,402 A | 11/1994 | Conway et al. |
| 5,370,656 A | 12/1994 | Shevel |
| 5,370,899 A | 12/1994 | Conway et al. |
| 5,374,261 A | 12/1994 | Yoon |
| 5,392,787 A | 2/1995 | Yoon |
| 5,397,302 A | 3/1995 | Weaver et al. |
| 5,407,423 A | 4/1995 | Yoon |
| 5,417,671 A | 5/1995 | Jackson |
| 5,423,745 A | 6/1995 | Todd et al. |
| 5,429,127 A | 7/1995 | Kolobow |
| 5,439,457 A | 8/1995 | Yoon |
| 5,443,063 A | 8/1995 | Greenberg |
| 5,447,505 A | 9/1995 | Valentine et al. |
| 5,451,204 A | 9/1995 | Yoon |
| 5,452,715 A | 9/1995 | Boussignac |
| 5,466,231 A | 11/1995 | Cercone et al. |
| 5,469,864 A | 11/1995 | Rosenblatt |
| 5,482,740 A | 1/1996 | Conway et al. |
| 5,484,426 A | 1/1996 | Yoon |
| 5,487,730 A | 1/1996 | Marcadis et al. |
| 5,490,839 A | 2/1996 | Wang et al. |
| 5,494,029 A | 2/1996 | Lane et al. |
| 5,496,276 A | 3/1996 | Wang et al. |
| 5,501,669 A | 3/1996 | Conway et al. |
| 5,507,284 A | 4/1996 | Daneshvar |
| 5,509,899 A | 4/1996 | Fan et al. |
| 5,524,642 A | 6/1996 | Rosenblatt |
| 5,545,132 A | 8/1996 | Fagan et al. |
| 5,556,391 A | 9/1996 | Cercone et al. |
| 5,593,718 A | 1/1997 | Conway et al. |
| 5,599,292 A | 2/1997 | Yoon |
| 5,599,299 A | 2/1997 | Weaver et al. |
| 5,599,321 A | 2/1997 | Conway et al. |
| 5,611,336 A | 3/1997 | Page et al. |
| 5,613,950 A | 3/1997 | Yoon |
| 5,649,902 A | 7/1997 | Yoon |
| 5,653,229 A | 8/1997 | Greenberg |
| 5,670,111 A | 9/1997 | Conway et al. |
| 5,674,192 A | 10/1997 | Sahatjian et al. |
| 5,693,014 A | 12/1997 | Abele et al. |
| 5,694,922 A | 12/1997 | Palmer |
| 5,697,365 A * | 12/1997 | Pell .......................... 128/207.15 |
| 5,700,239 A | 12/1997 | Yoon |
| 5,714,110 A | 2/1998 | Wang et al. |
| 5,715,815 A | 2/1998 | Lorenzen et al. |
| 5,720,726 A | 2/1998 | Marcadis et al. |
| 5,722,931 A | 3/1998 | Heaven |
| 5,730,123 A | 3/1998 | Lorenzen |
| 5,733,252 A | 3/1998 | Yoon |
| 5,735,271 A | 4/1998 | Lorenzen et al. |
| 5,738,901 A | 4/1998 | Wang et al. |
| 5,765,559 A | 6/1998 | Kim |
| 5,769,882 A | 6/1998 | Fogarty et al. |
| 5,803,908 A | 9/1998 | Steuer et al. |
| 5,810,786 A | 9/1998 | Jackson et al. |
| 5,819,733 A | 10/1998 | Bertram |
| 5,827,215 A | 10/1998 | Yoon |
| 5,843,017 A | 12/1998 | Yoon |
| 5,843,028 A | 12/1998 | Weaver et al. |
| 5,843,060 A | 12/1998 | Cercone |
| 5,843,089 A | 12/1998 | Sahatjian et al. |
| 5,868,719 A | 2/1999 | Tsukernik |
| 5,908,406 A | 6/1999 | Ostapchenko et al. |
| 5,951,597 A | 9/1999 | Westlund et al. |
| 5,954,706 A | 9/1999 | Sahatjian |
| 5,954,740 A | 9/1999 | Ravenscroft et al. |
| 5,971,954 A | 10/1999 | Conway et al. |
| 5,976,072 A | 11/1999 | Greenberg |
| 5,997,503 A | 12/1999 | Willis et al. |
| 5,997,546 A | 12/1999 | Foster et al. |
| 6,010,480 A | 1/2000 | Abele et al. |
| 6,012,451 A | 1/2000 | Palmer |
| 6,048,332 A | 4/2000 | Duffy et al. |
| 6,110,192 A | 8/2000 | Ravenscroft et al. |
| 6,129,547 A | 10/2000 | Cise |
| 6,132,824 A | 10/2000 | Hamlin |
| 6,152,136 A | 11/2000 | Pagan |
| 6,169,123 B1 | 1/2001 | Cercone |
| 6,210,364 B1 | 4/2001 | Anderson |
| 6,213,975 B1 | 4/2001 | Laksin |
| 6,214,895 B1 | 4/2001 | Cercone |
| 6,227,200 B1 | 5/2001 | Crump et al. |
| 6,240,321 B1 | 5/2001 | Janke et al. |
| 6,248,088 B1 | 6/2001 | Yoon |
| 6,264,631 B1 | 7/2001 | Willis et al. |
| 6,264,633 B1 | 7/2001 | Knorig |
| 6,277,089 B1 | 8/2001 | Yoon |
| 6,312,421 B1 | 11/2001 | Boock |
| 6,322,586 B1 | 11/2001 | Monroe et al. |
| 6,328,710 B1 | 12/2001 | Wang et al. |
| 6,364,856 B1 | 4/2002 | Ding et al. |
| 6,378,521 B1 | 4/2002 | Van Den Berg |

(56) References Cited

U.S. PATENT DOCUMENTS

| | | |
|---|---|---|
| 6,394,093 B1 | 5/2002 | Lethi |
| 6,395,012 B1 | 5/2002 | Yoon et al. |
| 6,398,266 B1 | 6/2002 | Crump |
| 6,409,716 B1 | 6/2002 | Sahatjian et al. |
| 6,481,436 B1 | 11/2002 | Neame |
| 6,494,203 B1 | 12/2002 | Palmer |
| 6,501,945 B1 | 12/2002 | Chien |
| 6,524,274 B1 | 2/2003 | Rosenthal et al. |
| 6,526,977 B1 | 3/2003 | Göbel |
| 6,543,451 B1 | 4/2003 | Crump et al. |
| 6,551,272 B2 | 4/2003 | Gobel |
| 6,572,813 B1 | 6/2003 | Zhang et al. |
| 6,584,970 B1 | 7/2003 | Crump et al. |
| 6,588,425 B2 | 7/2003 | Rouns et al. |
| 6,588,427 B1 | 7/2003 | Carlsen et al. |
| 6,602,218 B2 | 8/2003 | Yoon |
| 6,602,219 B2 | 8/2003 | Madsen et al. |
| 6,609,520 B1 | 8/2003 | Carlsen et al. |
| 6,612,304 B1 | 9/2003 | Cise et al. |
| 6,612,305 B2 | 9/2003 | Fauza |
| 6,613,025 B1 | 9/2003 | Palasis |
| 6,615,835 B1 | 9/2003 | Cise et al. |
| 6,620,128 B1 | 9/2003 | Simhambhatla |
| 6,623,450 B1 | 9/2003 | Dutta |
| 6,629,530 B2 | 10/2003 | Cise |
| 6,632,091 B1 | 10/2003 | Cise et al. |
| 6,651,664 B1 | 11/2003 | Lomholt |
| 6,687,519 B2 | 2/2004 | Steuer et al. |
| 6,688,306 B1 | 2/2004 | Cise et al. |
| 6,698,424 B2 | 3/2004 | Madsen et al. |
| 6,705,320 B1 | 3/2004 | Anderson |
| 6,722,368 B1 | 4/2004 | Shaikh |
| 6,726,696 B1 | 4/2004 | Houser et al. |
| 6,745,773 B1 | 6/2004 | Gobel |
| 6,767,340 B2 | 7/2004 | Willis et al. |
| 6,769,430 B1 | 8/2004 | Carlsen et al. |
| 6,770,066 B1 | 8/2004 | Weaver et al. |
| 6,786,876 B2 | 9/2004 | Cox |
| 6,790,221 B2 | 9/2004 | Monroe et al. |
| 6,796,309 B2 | 9/2004 | Nash et al. |
| 6,802,317 B2 | 10/2004 | Göbel |
| 6,805,125 B1 | 10/2004 | Crump et al. |
| 6,808,521 B1 | 10/2004 | McMichael |
| 6,814,730 B2 | 11/2004 | Li |
| 6,890,339 B2 | 5/2005 | Sahatjian et al. |
| 6,908,449 B2 | 6/2005 | Willis et al. |
| 6,916,307 B2 | 7/2005 | Willis et al. |
| 6,923,786 B2 | 8/2005 | Rouns et al. |
| 6,979,420 B2 | 12/2005 | Weber |
| 6,997,909 B2 | 2/2006 | Goldberg |
| 6,997,918 B2 | 2/2006 | Soltesz et al. |
| 7,040,321 B2 | 5/2006 | Gobel |
| 7,040,322 B2 | 5/2006 | Fortuna |
| 7,056,466 B2 | 6/2006 | Wang et al. |
| 7,066,905 B2 | 6/2006 | Squire et al. |
| 7,073,503 B2 | 7/2006 | Lomholt |
| 7,096,868 B2 | 8/2006 | Tateo et al. |
| 7,147,252 B2 | 12/2006 | Teuscher et al. |
| 7,258,120 B2 | 8/2007 | Melker |
| 8,196,584 B2 | 6/2012 | Maguire et al. |
| 2001/0041861 A1 | 11/2001 | Gobel |
| 2002/0077603 A1 | 6/2002 | Willis et al. |
| 2002/0077604 A1 | 6/2002 | Willis et al. |
| 2002/0078960 A1 | 6/2002 | Cise |
| 2002/0078963 A1 | 6/2002 | Rouns et al. |
| 2002/0082552 A1 | 6/2002 | Ding et al. |
| 2002/0091375 A1 | 7/2002 | Sahatjian et al. |
| 2002/0110657 A1 | 8/2002 | Wang et al. |
| 2002/0150707 A1 | 10/2002 | Wilkons |
| 2002/0193753 A1 | 12/2002 | Rouns et al. |
| 2002/0195110 A1 | 12/2002 | Watton |
| 2003/0000526 A1 | 1/2003 | Gobel |
| 2003/0032407 A1 | 2/2003 | Mages |
| 2003/0066532 A1 | 4/2003 | Gobel |
| 2003/0069620 A1 | 4/2003 | Li |
| 2003/0111077 A1 | 6/2003 | Hooser et al. |
| 2003/0116162 A1 | 6/2003 | Madsen et al. |
| 2003/0116963 A1 | 6/2003 | Teuscher et al. |
| 2003/0225369 A1 | 12/2003 | McMichael et al. |
| 2003/0225392 A1 | 12/2003 | McMichael et al. |
| 2003/0225393 A1 | 12/2003 | McMichael et al. |
| 2004/0024363 A1 | 2/2004 | Goldberg |
| 2004/0079376 A1 | 4/2004 | Melker |
| 2004/0092870 A1 | 5/2004 | Squire et al. |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0116898 A1 | 6/2004 | Hawk |
| 2004/0122110 A1 | 6/2004 | MacCabee et al. |
| 2004/0154623 A1 | 8/2004 | Schaeffer et al. |
| 2004/0193100 A1 | 9/2004 | Van Hooser et al. |
| 2004/0193101 A1 | 9/2004 | Van Hooser et al. |
| 2004/0215142 A1 | 10/2004 | Matheis et al. |
| 2004/0220534 A1 | 11/2004 | Martens et al. |
| 2004/0221853 A1 | 11/2004 | Miller |
| 2004/0255952 A1 | 12/2004 | Carlsen et al. |
| 2005/0004560 A1 | 1/2005 | Cox |
| 2005/0033267 A1 | 2/2005 | Decaria |
| 2005/0033268 A1 | 2/2005 | Decaria |
| 2005/0033269 A1 | 2/2005 | Decaria |
| 2005/0038381 A1 | 2/2005 | McMichael |
| 2005/0065468 A1 | 3/2005 | Goebel |
| 2005/0124932 A1 | 6/2005 | Foster et al. |
| 2005/0124935 A1 | 6/2005 | McMichael |
| 2005/0137619 A1 | 6/2005 | Schewe et al. |
| 2005/0166924 A1 | 8/2005 | Thomas et al. |
| 2006/0118121 A1 | 6/2006 | Martens et al. |
| 2006/0118122 A1 | 6/2006 | Martens et al. |
| 2007/0095351 A1 | 5/2007 | Gobel |
| 2007/0289596 A1 | 12/2007 | Campbell et al. |
| 2007/0295336 A1 | 12/2007 | Nelson et al. |
| 2007/0295337 A1* | 12/2007 | Nelson et al. ............ 128/207.15 |
| 2007/0296125 A1 | 12/2007 | Colburn et al. |
| 2008/0064839 A1 | 3/2008 | Hadba et al. |
| 2008/0072911 A1 | 3/2008 | Flagler et al. |
| 2008/0078400 A1 | 4/2008 | Martens et al. |
| 2008/0078403 A1* | 4/2008 | Clayton ................... 128/207.15 |
| 2008/0078405 A1* | 4/2008 | Crumback et al. ....... 128/207.15 |
| 2008/0125711 A1 | 5/2008 | Alpini et al. |

FOREIGN PATENT DOCUMENTS

| | | |
|---|---|---|
| CN | 2540984 Y | 3/2003 |
| DE | 19500550 | 11/1994 |
| DE | 19500550 | 7/1996 |
| DE | 19855521 | 6/2000 |
| EP | 0214721 | 3/1987 |
| EP | 0884061 | 6/1998 |
| EP | 0 884 061 | 12/1998 |
| EP | 1005877 | 6/2000 |
| EP | 1135184 | 6/2000 |
| EP | 1267981 | 1/2003 |
| GB | 1313347 | 4/1973 |
| GB | 2168256 | 11/1985 |
| GB | 2168256 | 6/1986 |
| WO | WO 95/22367 | 8/1995 |
| WO | WO 9522367 | 8/1995 |
| WO | WO 00/27461 | 5/2000 |
| WO | WO 00/32262 | 6/2000 |
| WO | WO 00/32263 | 6/2000 |
| WO | WO 03/045487 | 6/2003 |
| WO | WO 2004/067262 | 8/2004 |
| WO | WO 2004067262 | 8/2004 |
| WO | WO 2004/101046 | 11/2004 |
| WO | WO 2006/023486 | 3/2006 |
| WO | WO 2007/140262 | 6/2007 |
| WO | WO 2007/149202 | 12/2007 |

OTHER PUBLICATIONS

Ayşe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).

(56) References Cited

OTHER PUBLICATIONS

Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.

Dullenkopf, et al., "Fluid leakage past tracheal tube cuffs: evaluation on the new Microcuff endotracheal tube," Intensive Care Medicine, (2003) vol. 29, pp. 1849-1853.

Sartomer Application Bulletin; "Functional Acrylic Monomers as Modifiers for PVC Plastisol Formulations," pp. 1-6.

Shintani; "Modification of Medical Device Surface to Attain Anti-Infection," National Institute of Health Sciences; Trends Biomater. Artif. Organs, vol. 18(1), pp. 1-8 (2004).

Tecogel brochure page, Noveon Thermedics Polymer Products, Oct. 2003.

* cited by examiner

CUFF FOR USE WITH MEDICAL TUBING AND METHOD AND APPARATUS FOR MAKING THE SAME

BACKGROUND

The present disclosure relates to medical devices, and more particularly, to tracheal tubes and other tubes designed to form a seal against a surrounding passage.

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Within the course of medical treatment, a tube or other medical device may sometimes be used to control the flow of air, food, fluids, or other substances into a patient. For example, medical devices (such as various types of tubes and catheters) may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal tubes or tracheostomy tubes. To create a seal between such tubes and the tracheal wall, an inflatable cuff is typically employed. When inflated, the cuff may prevent air from flowing into or out of the patient's lungs except via the tube. In this manner, major air leaks during positive pressure ventilation, i.e., when air is being pushed into the lungs, and gas leaks during anesthesia procedures may be prevented.

The cuffs employed on devices such as endotracheal tubes or tracheostomy tubes may be manufactured from a variety of polymeric compositions, such as polyurethane (PU) or polyvinyl chloride (PVC). It may be desirable to manufacture such cuffs while wasting as little of the polymeric composition as possible and/or to improve the efficiency of the manufacturing process.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A variety of medical devices are designed to be inserted within cavities or passages of the human body. Examples of such medical devices include catheters, stents, feeding tubes, intravenous tubes, breathing tubes, and so forth. In many instances it is desirable that the device be provided with an inflatable cuff that can be used to form a seal between the medical device and the surrounding passage or cavity. In accordance with aspects of the present disclosure, such a cuff may be manufactured using more than one mold (either in series or in parallel) and/or using molds having more than one cuff-shaped cavity such that more than one cuff may be formed in each molding operation. In addition to increasing the number of cuffs formed in each operation, such an approach may also increase the number of cuffs that can be produced using a given length of tubing material. In this manner, the number of cuffs produced per molding operation may be increased and/or the amount of tubing material wasted (i.e., not being used to form a cuff) may be decreased.

Figures 1, 2:
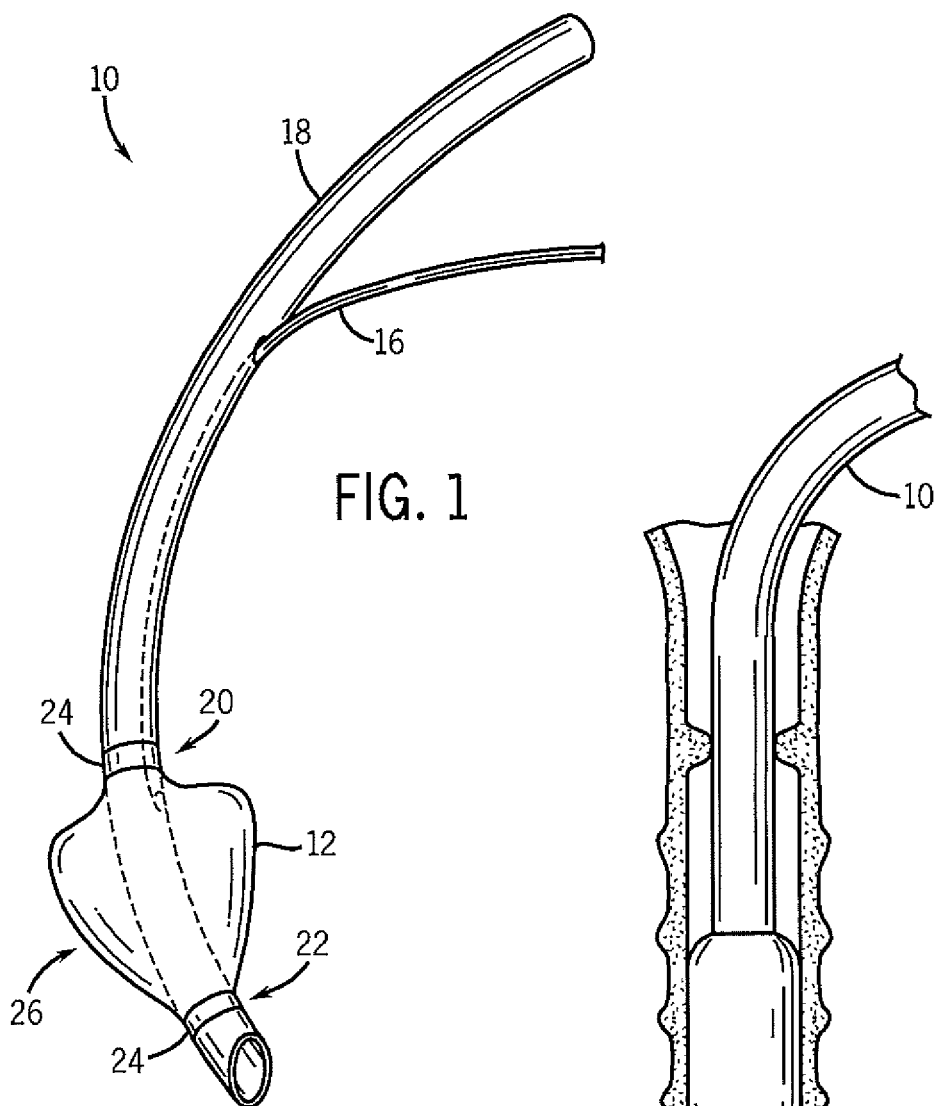
FIG. 1 illustrates a tracheal tube, in accordance with aspects of the present disclosure.
FIG. 2 illustrates a tracheal tube deployed within a trachea, in accordance with aspects of the present disclosure.

With the foregoing in mind, an example of a medical device that may include a cuff is an endotracheal tube 10, as depicted in FIG. 1. The endotracheal tube 10 includes an inflatable cuff 12 that may be inflated at low pressure (approximately 25 cm $H_2O$ or less) to form a seal against the trachea wall 14 (see FIG. 2). Typically the inflatable cuff 12 is inflated and deflated via a tube 16 in communication with the inflatable cuff 12.

For simplicity, the present example describes the use of an inflatable cuff 12 in the context of an endotracheal tube. However, an inflatable cuff 12 may be used with other medical devices, such as those listed above, or with other devices in which it is desirable to form a seal between the device and a surrounding passage or pathway. Therefore, it should be understood that the present examples and descriptions are merely exemplary and are not intended to limit the scope of the present disclosure.

Returning now to FIG. 1, in accordance with the one embodiment, the wall of the inflatable cuff 12 is about 0.00086 inches (0.022 mm) thick or less. In addition, the walls of the inflatable cuff 12 are made of a material having suitable mechanical properties (such as puncture resistance, tear resistance, pin hole resistance, tensile strength), chemical properties (such as forming a suitable bond to the main tube body 18), and biocompatibility.

In one embodiment, the walls of the inflatable cuff 12 are made of a polyurethane or polyurethane-based composition having suitable mechanical and chemical properties. An example of one suitable polyurethane is Dow Pellethane® 2363-90AE. In other embodiments, the walls of the inflatable cuff 12 are made of other suitable compositions, such as compositions having suitable mechanical properties at the desired wall thickness of the cuff 12. Examples of suitable polymeric compositions may include polymethylmethacrylate (PMMA), polyacrylonitrile (PAN), polyamide (such as nylon) (PA), polycarbonate (PC), polyesters (such as polyethylene terephthalate (PET)), polyolefins (such as polyethylenes (PE) and polypropylenes (PP)), polystyrene (PS) or vinyls (such as polyvinyl chloride (PVC) and polyvinylacetate). Other polymers and/or polymer admixtures having suitable mechanical, chemical, and biocompatibility properties may also be used to form the cuff 12.

In the embodiment depicted in FIG. 1, the cuff 12 is shaped as being generally tapered, being wider at one end when inflated. As will be appreciated by those of ordinary skill in the art, the degree of taper, curvature and/or linearity at different parts of the cuff 12 may vary. As depicted in the embodiment of FIG. 1, the cuff 12 may be secured at the proximate end 20 and distal end 22 to the main tube body 18, such as by collar regions 24 adhered, fused, or otherwise attached to the main tube body 18. However, the cuff body 26 between the proximate end 20 and the distal end 22 forms an expanded structure between these ends when partially or completely inflated. As depicted in FIG. 2, when inflated in the trachea, portions of the inflated cuff 12 may be partially flattened against the trachea wall to form a seal against the tracheal wall 14.

While the cuff 12 in FIG. 1 is depicted as tapered when inflated, in various exemplary embodiments the inflatable cuff 12 may be shaped differently when inflated. For example, the cuff may be tapered differently or opposite to what is depicted in FIG. 1, or may be generally symmetrical, without a substantial taper from one end to the other. Likewise, other cuff shapes having straight walls, curved walls, or combinations of straight and curved walls are possible and are within the scope of the present disclosure. The collar regions 24 adhering or otherwise attaching the various cuffs to the respective main tube bodies 18 are typically the same or about the same diameter as the main tube body 18.

The inflatable cuffs 12 discussed herein may be formed by various techniques. In one implementation, the inflatable cuff 12 is formed by blow-molding. For example, in one such implementation a preformed tubular polyurethane extrusion is blow-molded to form the cuff 12. The tubular extrusion has a suitable internal diameter and wall thickness such that, when the extrusion is blown, the resulting cuff 12 has a sufficient internal diameter to fit onto an endotracheal tube 10 and has the desired wall thickness.

Figure 3:
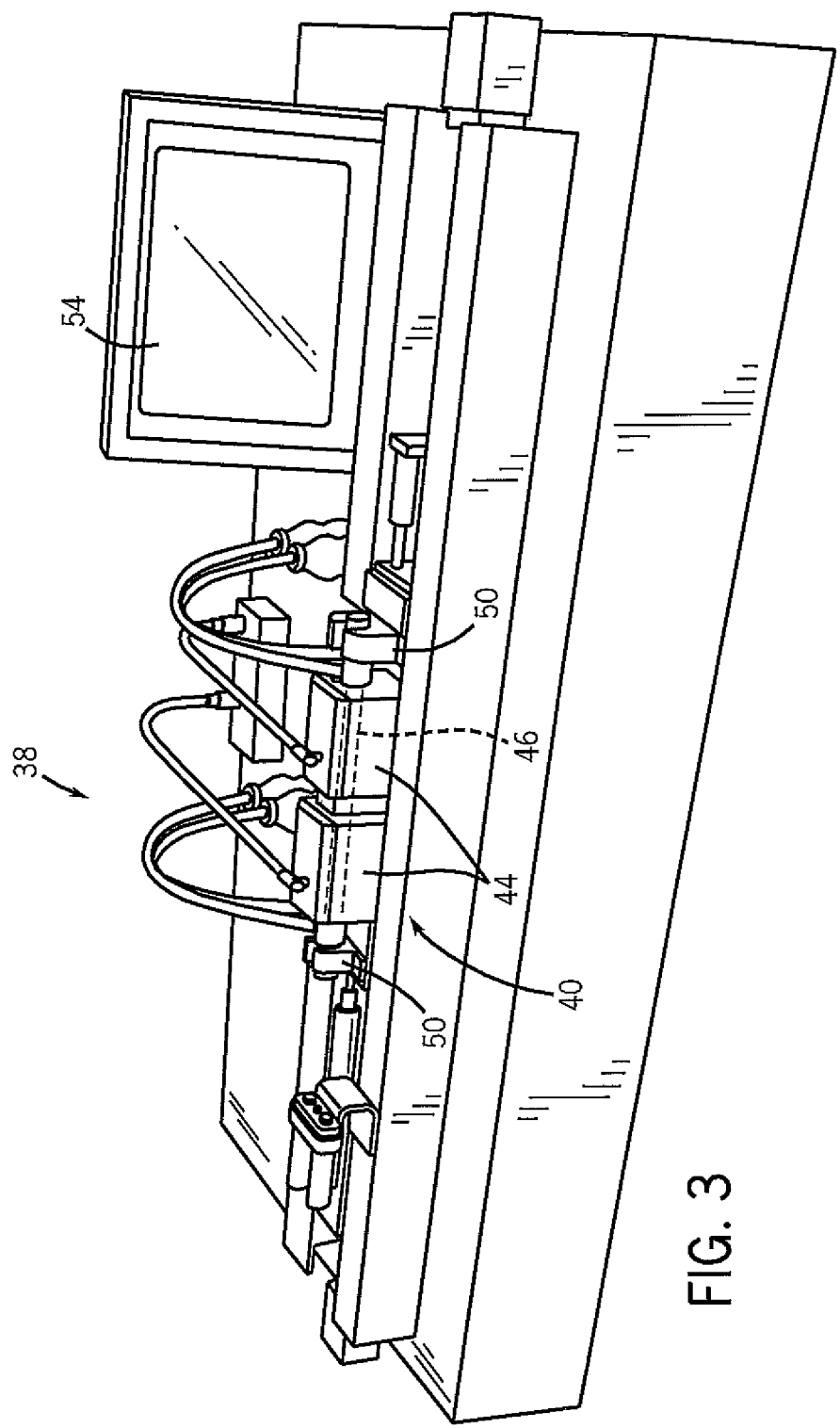
FIG. 3 illustrates a blow molding machine, in accordance with aspects of the present disclosure.

For example, a tube, such as a preformed extruded polyurethane tube, may be loaded into a mold assembly 40 of a blow molding machine 38, as depicted in FIG. 3. A suitable blow molding machine 38, such as an angioplasty balloon blowing machine, may allow process parameters such as the stretch of the preformed tube, blow pressure, and temperature to be controlled. In one embodiment, the blow molding machine 38 may be a model 2210 computerized balloon forming machine, available from Interface Associates, which is configured to run at 1-2 bars of gas pressure.

In an embodiment, the mold assembly 40 may include two or more molds 42 (FIGS. 5-11) housed (serially and/or parallel to one another) within common or separate heating/cooling jackets 44. In one embodiment, the molds 42 may be manufactured from beryllium copper and may be split horizontally to allow opening and closing of the mold 42 when not in the respective jacket 44. The heating/cooling jackets 44 may house one or more molds 42 as well as components for heating and/or cooling the molds 42. For example, the heating/cooling jackets 44 may include passages, conduits, or open areas through which coolant (such as cooled water) may flow to actively cool the molds 42. In addition, the heating/cooling jackets 44 may include one or more heating cartridges or other heating elements (such as resistive heating elements which heat when a current is passed through the element) which may be used to actively heat the molds 42. For example, in one embodiment, the heating/cooling jacket 44 includes a series of ten electrical heating elements used to heat the molds 42. In this manner, the heating/cooling jackets 44 may actively regulate the temperature of the molds 42 contained within.

The mold assembly 40 may be bracketed on either side by clamp structures 50 that secure respective ends of the tube 46 when placed within the mold assembly 40. One or both of the clamp structures 50 may include nozzles which are secured within the end of the tube 46 when clamped and which allow a gas (such as nitrogen) to be injected at pressure into the secured tube 46. In one embodiment, the clamp structures 50 may move outward with respect to the mold assembly 40 such that a secured tube 46 may be placed under tension.

In one implementation, a length of tube 46 which is inserted into the mold assembly 40 and secured by the clamps 50 may be approximately 12 inches (30.48 cm) in length prior to being placed under tension. In general, the tube 46 may be between about 10 to about 12 inches (i.e., approximately 25 cm to 30 cm) in length when inserted into the mold assembly 40 and secured by the clamp structures 50 prior to application of tension. In one embodiment, the end-portions of the extruded tube 46 that project out from the mold 42 are constrained to the shape and thickness of the original extruded tube by non-heat transferable plastic holders at the ends of the mold 42.

As depicted, the blow molding machine 38 may include a control station 54, which may include a user interface and/or controls, a monitor, and so forth. The control station 54 may display current status information for a blow molding operation and/or may display a user interface with which a user can interact to select, initiate, and/or control one or more programs or operations to be performed by the blow molding machine 38. Such programs or operations may coordinate operation of the clamps 50 in applying tension to a tube 46, may control heating and cooling of the jackets 44 such that a particular temperature profile is achieved with respect to the mold 42 over time, and may control injection of pressurized gas into the tube 46 as part of a blow molding process.

In one embodiment, the control station 54 may include a touch sensitive screen by which the user interacts with the interface, though in other embodiments, a keyboard and mouse or other similar interface may contain buttons or keys by which the user interacts with the displayed user interface.

In one embodiment, the control station 54 may be a programmed computer configured to display a user interface and status information, to receive user commands, and to control operation of other components of the blow molding machine 38. In other embodiments, the control station 54 may be any suitable processor based system or components configured to perform some or all of these functions. Such computers or other processor based systems may include one or more processors as well as memory and storage components suitable for storing and executing routines and/or programs as discussed above for controlling operation of different components of the blow molding machine 38.

Figure 4:
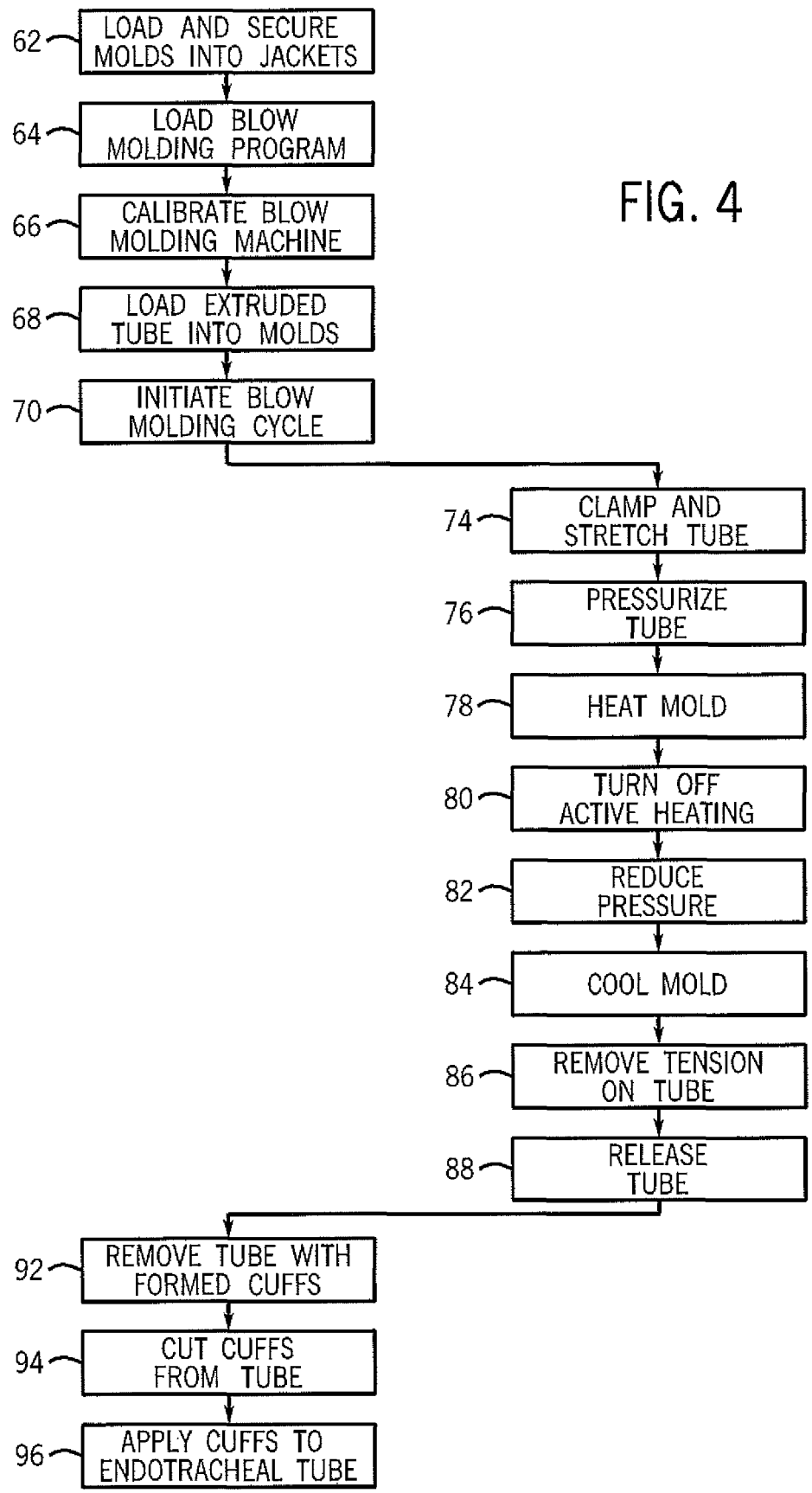
FIG. 4 is a flow chart depicting acts for manufacturing inflatable cuffs, in accordance with aspects of the present disclosure.

With the foregoing in mind, and turning now to FIG. 4, a flowchart is depicted setting forth a method 60 for forming cuffs for a medical device in accordance with one embodiment of the present disclosure. In this method 60, two or more molds 42 (FIG. 3) are loaded and secured (block 62) within one or more respective heating/cooling jackets 44. For example, the molds 42 may be loaded into the respective jacket or jackets 44 and pneumatically locked into place once loaded. In one embodiment, the molds 42 may be loaded in series (i.e., end-to-end) within a common jacket 44 or in separate respective jackets 44. In other embodiments, the molds 42 may be loaded in parallel (i.e., side-by-side) within a common jacket 44 or in separate respective jackets 44. In another embodiment, four or more molds 42 may be employed and may be loaded and secured in a common jacket 44 or in separate respective jackets 44 in both series and parallel configurations, i.e., some of the molds 42 may be situated end-to-end while also being side-by-side with other molds 42.

In the depicted method 60, a blow molding program is loaded (block 64) to a blow molding machine 38, such as via operation of the control station 54. The blow molding program may control a cycle of operation of the blow molding machine 38 during which two or more cuffs will be formed using the loaded molds 42. For example, in one embodiment, the loaded program may control the extent to which one or more preformed tubes are stretched, the temperature profile to which the tubes are subjected, and/or the pressure at which gas, such as nitrogen, is injected into the tubes, as well as the timing of such actions.

The blow molding machine 38 may also be calibrated (block 66) or zeroed out prior to beginning a blow molding operation. For example, the molds 42, jackets 44, and/or clamps 50 may be positioned at a start location, the temperature of the jackets may be set at an initial temperature or measured for use as a start point, and so forth. One or more tubes 46 may then be loaded (block 68) into each set of molds 42 (e.g., into the collet/mandrel system of the respective molds) provided in series. In one embodiment, a 12 inch (30.48 cm) long preformed tube 46 of polyurethane is loaded into two molds 42 placed end-to-end. For example, in one embodiment, a commercially available pre-formed extrusion of Dow Pellethane® 2363-90AE having an inner diameter between 0.1708 inches and 0.296 inches (4.34 mm to 7.52 mm) and a wall thickness of about 0.20 inches±0.05 inches (5.08 mm±1.27 mm) may be loaded into the molds 42 and blown to form cuffs 12 suitable for use with a 7.5 mm internal diameter (ID) endotracheal tube. In certain embodiments where molds 42 are loaded in parallel, more than one tube 46 may be loaded into the respective molds 42, i.e., each set of parallel molds 42 may be loaded with a separate tube 46.

An operator may initiate (block 70) a blow molding operation on the blow molding machine 38, such as by actuating one or more buttons or switches, or by interacting with an initiation option at the control station 54. As will be appreciated, the foregoing steps may be performed in the described order or in a different order, depending on the implementation. For example, the blow molding program may be loaded (block 64) prior to loading and securing (block 62) the molds 42, and so forth.

In the depicted example, the loaded tube 46 is clamped on the ends of the tube 46 by the clamps 50. At least one end of the tube 46 is clamped around a nozzle inserted into the tube end. In one implementation, the clamps 50 are initially spaced apart from the ends of the tube 46 and move inward, such as 50 mm, to reach the tube ends and to clamp the tube ends. Once clamped to the tube ends, the clamps 50 may move outward from the respective molds 42 to linearly stretch (block 74) the clamped tube 46. In one embodiment, the clamps 50 each move outward 100 mm to 120 mm (for a total stretch of 200 mm to 240 mm) and hold the tube 46 under tension at this position. In one implementation, the operator initiates the stretch operation by actuating one or more buttons or switches or by interacting with an initiation option at the control station 54.

In the depicted example, the tube 46 is pressurized (block 76), such as with pressurized nitrogen. For example, pressurized nitrogen (or other gas) may be blown into the tube via a nozzle or nozzles inserted into the ends of the tube 46 such that the clamps 50 hold the respective end or ends of the tube 46 around the respective nozzle or nozzles. The nozzle may be connected to a source of pressurized air, such as an air pump or pre-pressurized source, to achieve a desired positive pressure within the tube 46 and to blow out the cuff walls to the shape of the mold 42. In one embodiment, nitrogen is blown into the tube 46 to produce a pressure of about 1.2 bar to about 1.6 bar within the tube 46. In one implementation, the pressure may be increased to 1.6 bar and then decreased to 1.4 bar after the initial pressure is reached.

As the pressure is increased, the molds 42 may be heated (block 78), such as by activating the heater cartridges within the heating/cooling jacket(s) 44. In one embodiment, the temperature of the mold 42 is quickly raised from an initial temperature of 50° C. to 80° C. and may continue to rise to 120° C. In one implementation, at the pressure/temperature changeover point the pressure in the tube 46 may be reduced to 1.3 bar while the temperature rises to 120° C. Once a desired temperature and pressure is reached, the tube 46 may be held at this temperature and pressure for a set time interval, such as between 60 and 90 seconds. Tension on the tube 46 may be relaxed during the heating process (e.g., moving the clamps 50 inward to 50 mm from 120 mm of pull) or the tube 46 may be maintained under full tension throughout the heating process.

In the depicted example, the active heating of the mold is discontinued, i.e., turned off (block 80) after a desired temperature is reached and/or a set time has elapsed. For example, in one implementation heater cartridges in the heating/cooling jackets 44 are turned off when the molds 42 reach 120° C. However, the temperature of the molds 42 may continue to rise after the heating cartridges are turned off. In one such example, the heater cartridges may be turned off and, over a dwell time of approximately 8 seconds, the temperature of the molds 42 may continue to rise to approximately 130° C.

After the dwell time and/or after a desired maximum temperature is reached, the pressure within the tube 46 may be reduced (block 82). For example, in one embodiment, nitrogen pressure may be reduced to 1 bar. In one embodiment, coolant, such as cooled water, may be flushed through conduits in the heating/cooling jacket 44 to actively cool (block 84) the mold 42 once the dwell time is finished and the pressure has been reduced. For example, the mold 42 may be cooled to approximately 55° C. in 10 to 15 seconds by active cooling. In one implementation, active cooling of the mold 42 may be stopped at 60° C., allowing the mold 42 to continue cooling to 55° C. without active cooling. In one embodiment, at 60° C. active cooling is stopped and a vacuum is applied to the heating/cooling jacket 44 to remove coolant. In such an embodiment, the temperature of the mold 42 may continue to drop to 55° C. Pressure applied to the interior of the tube 46 may also be reduced to 0 bar at this time in one such embodiment.

In the depicted embodiment, the tension may be removed (block 86) from the tube 46. For example, the clamps 50 holding the tube 46 may retract inwards relative to the mold assembly 40 such that the tube 46 is no longer under tension. In one such implementation, the clamps 50 may retract inwards to 50 mm on both sides and may release (block 88) the tube 46. Once released by the clamps 50, the tube 46 (which now includes two or more cuffs 12 in an implementation where molds 42 are arranged serially) may be removed (block 92) from the mold assembly 40. The tube 46 may then be cut (block 94) to produce the cuffs 12. In one embodiment, the cuffs 12 may have a wall thickness of approximately 30μ or less. Each cuff 12 may then be applied (block 96) to a respective endotracheal tube 10, as depicted in FIGS. 1 and 2. As will be appreciated, though the preceding discussion has been provided in the context of processing a preformed tube 46, in other embodiments the cuffs may be formed from a molten parison of extruded material (such as polyurethane) that is dropped into two or more mold apparatuses as discussed herein to undergo a blow molding process to form more than one cuff at a time.

Figure 5:
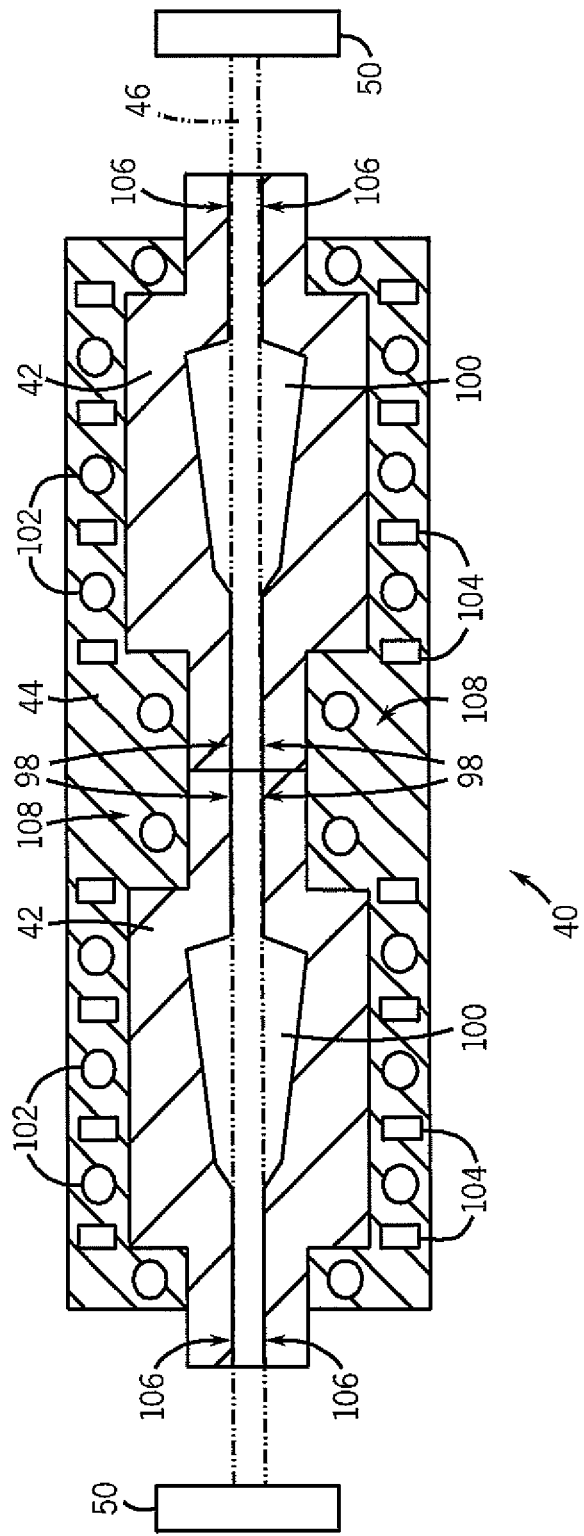
FIG. 5 depicts an embodiment of molds arranged in series in accordance with aspects of the present disclosure.

With the foregoing discussion in mind, FIGS. 5-11 depict in cross-section various embodiments of mold assemblies 40 suitable for use in a blow molding machine 38 and for producing two or more cuffs per blow molding operation. Turning to FIG. 5, two molds 42 are depicted in series, i.e., in an end-to-end arrangement. The molds have cavities 100 in the shape of the inflated cuff 12. In the depicted embodiment, the serially arranged molds 42 are disposed in a common heating/cooling jacket 44. In the depicted embodiment, the heating/cooling jacket 44 includes conduits 102 through which coolant, e.g., cooled water, may flow and electrical heating elements 104 which allow, respectively, active cooling and heating of the molds 42.

As will be appreciated, the depicted arrangement of conduits 102 and heating elements 104 is merely one possible arrangement. Other suitable arrangements of the conduits 102 and heating elements 104 may also be employed. For example, in one embodiment the heating elements 104 may be cylindrical in nature (as opposed to circular) and may run in the direction of the main axis of the heating/cooling jacket 44, i.e., in the direction the tube 46 is loaded. In such an embodiment, two or more such heating elements 104 may be spaced axially about the bore of the molds 42 to provide even heating. Likewise, the cooling conduits 102, may instead be provided as an open space or cavity surrounding some or all of the molds 42, such as an open cavity within the jacket 44. In such an embodiment, cooled water or other coolant may simply fill the cavity or be flushed through the cavity to achieve active cooling of the molds 42.

In the arrangement depicted in FIG. 5, a preformed tube 46 may be loaded into the mold assembly 40, allowing two cuffs 12 to be formed in the tube 46 during a single blow molding operation. For example, after being loaded into the mold assembly 40, the tube 46 may be clamped and placed under tension by the clamps 50, i.e., the clamps 50 may be moved outward from the mold assembly 40. An air nozzle inserted into one end of the tube 46 may blow nitrogen or other gases into the tube 46 under pressure such that the portions of the tube 46 in the cavities 100 blow out to contact the cavity walls. During or after the increase of pressure within the tube 46 the temperature of the molds 42 may be increased by activation of the heating elements 104 in the heating/cooling jacket 44. The heating elements 104 may be deactivated before or after the desired temperature and/or pressure are achieved. Once the desired temperature and/or pressure are achieved and maintained for a desired interval, the molds 42 may be cooled, such as by flushing coolant through the conduits 102 or a cavity of the heating/cooling jacket 44 and the pressure within the tube may be reduced. In addition, tension in the tube may be reduced or removed, such as by moving the clamps 50 inward toward the mold assembly. Upon release by the clamps 50, the tube 46 (including the newly formed cuff regions) may be removed from the mold assembly 40 for further processing.

Thus, in this manner, two (or more) cuffs 12 may be formed in a preformed tube 46 in a single blow molding operation. For example, for a 12 inch (30.48 cm) length of tube 46, two cuffs may be formed from the tube 46 in a single blow molding operation as opposed to a single cuff. In this manner, the number of cuffs produced in a given number of blow molding operations or in a given time period may be increased, e.g., doubled or more than doubled.

In one embodiment, the outside diameter of the tooling of the mold 42 may be reduced where the molds 42 are joined, such as at locations 98 of FIG. 5. For example, the outer diameter of the passage through the mold 42 at the locations 98 may be reduced relative to the outer diameter at locations 106 near the outside of the mold assembly. In such an embodiment, it may be desirable to have a reduced tooling outer diameter at locations 98 relative to locations 106 due to the tube 46 having a larger inner diameter/outer diameter at the locations 98 as a result of the temperature and pressure exerted on the tube 46 during a blow molding operation. In addition, in one embodiment the mold 42 may have cut-out regions 108 which may help prevent heat transfer between the molds 42, thereby resulting in a controllable internal diameter/outer diameter parameter.

Figure 6:
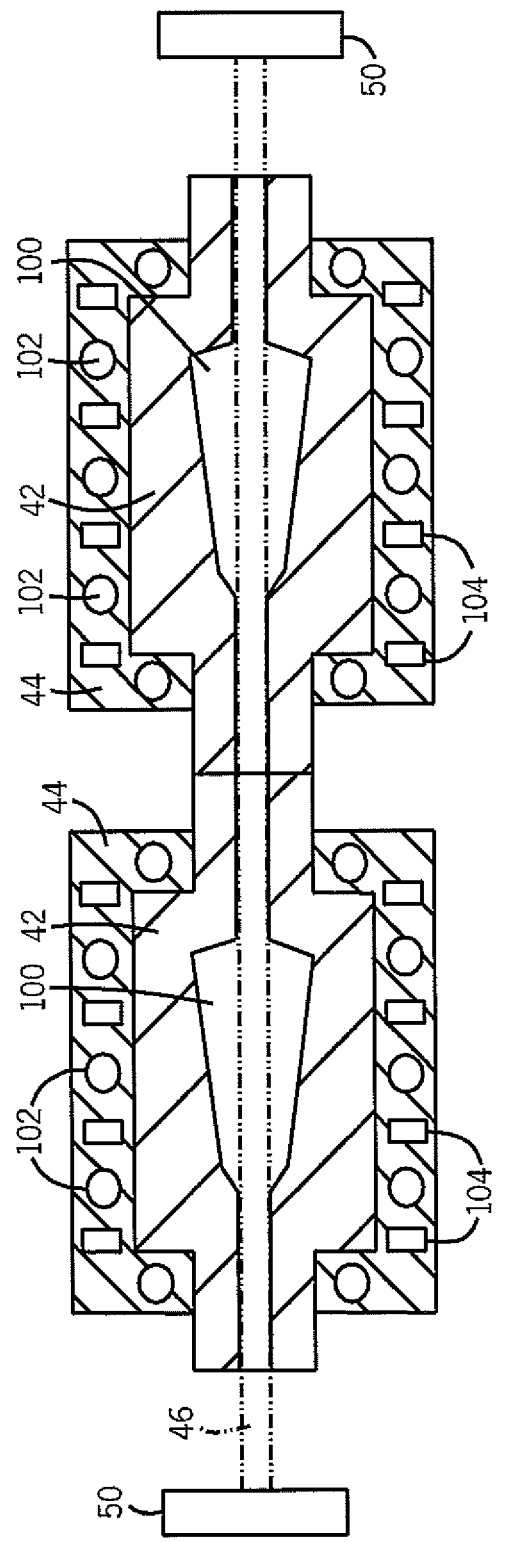
FIG. 6 depicts a further embodiment of molds arranged in series in accordance with aspects of the present disclosure.

Turning to FIG. 6, another serial arrangement of molds 42 is depicted. In this embodiment, instead of a common or shared heating/cooling jacket 44, separate heating/cooling jackets 44 are provided for each mold 42. Thus, the embodiment of FIG. 6 may be implemented using heating/cooling jackets 44 that are only configured to hold a single mold 42. In this manner, two (or more) cuffs 12 may be formed in a preformed tube 46 in a single blow molding operation using heating/cooling jackets 44 that are configured to hold only a single mold 42.

Figure 7:
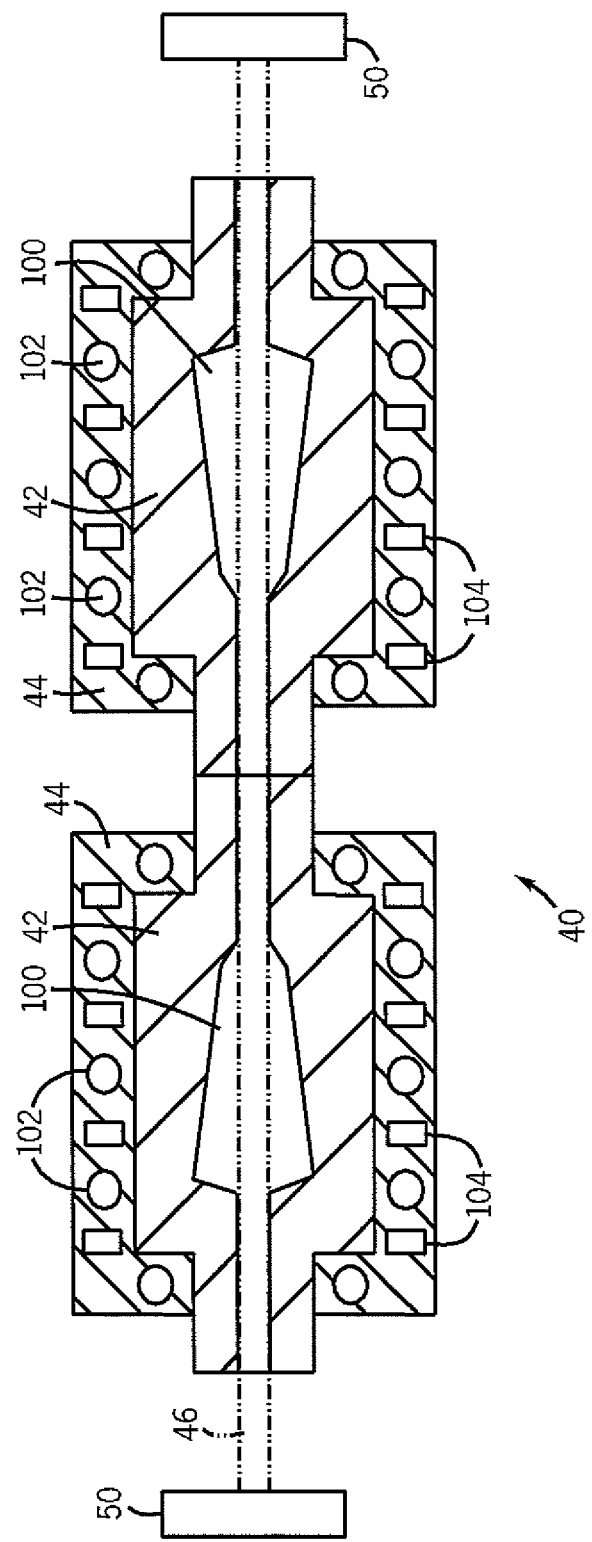
FIG. 7 depicts an additional embodiment of molds arranged in series in accordance with aspects of the present disclosure.

Likewise, FIG. 7 depicts a serial arrangement of molds 42 positioned within separate heating cooling jackets 44. Unlike the depicted embodiment of FIG. 6, the embodiment of FIG. 7 depicts the respective molds 42 in a symmetric, i.e., mirror image, relationship to one another. As will be appreciated, and as depicted in FIGS. 6 and 7, the relative orientation of the two or more molds 42 may or may not be symmetric, depending on a given implementation.

Figure 8:
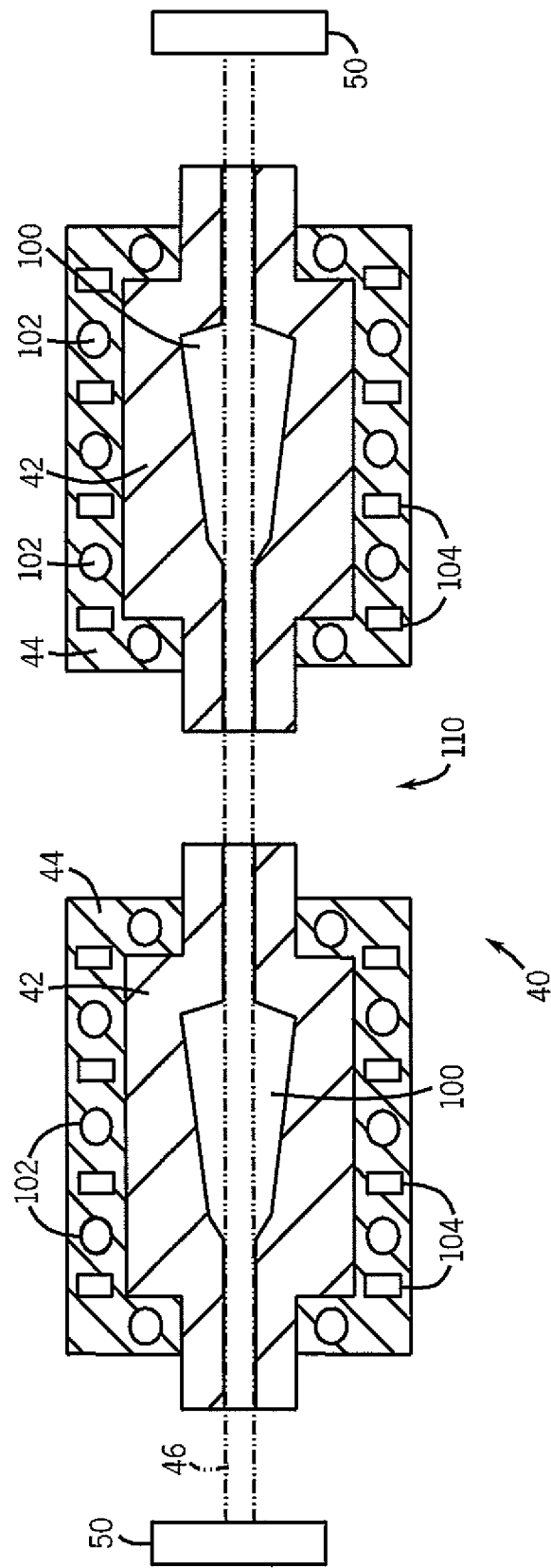
FIG. 8 depicts a further embodiment of molds arranged in series with a gap spacing the molds apart, in accordance with aspects of the present disclosure.

Unlike the embodiments depicted in FIGS. 5-7, the molds 42 may be spaced apart from one another, i.e., there is a gap 110 separating the molds 42, as depicted in the embodiment of FIG. 8. In such an embodiment, the separation of the molds 42 may prevent heat transfer between the molds 42, i.e., the gap 110 may thermally insulate the molds 42 from one another. Such thermal separation and/or independence of the molds 42 may be desirable. For example, in embodiments where different temperature profiles are applied to the molds 42 (e.g., where one mold 42 is heated to a different temperature and/or for a different interval than the other), the absence of heat transfer between the molds 42 may be desirable.

Figure 9:
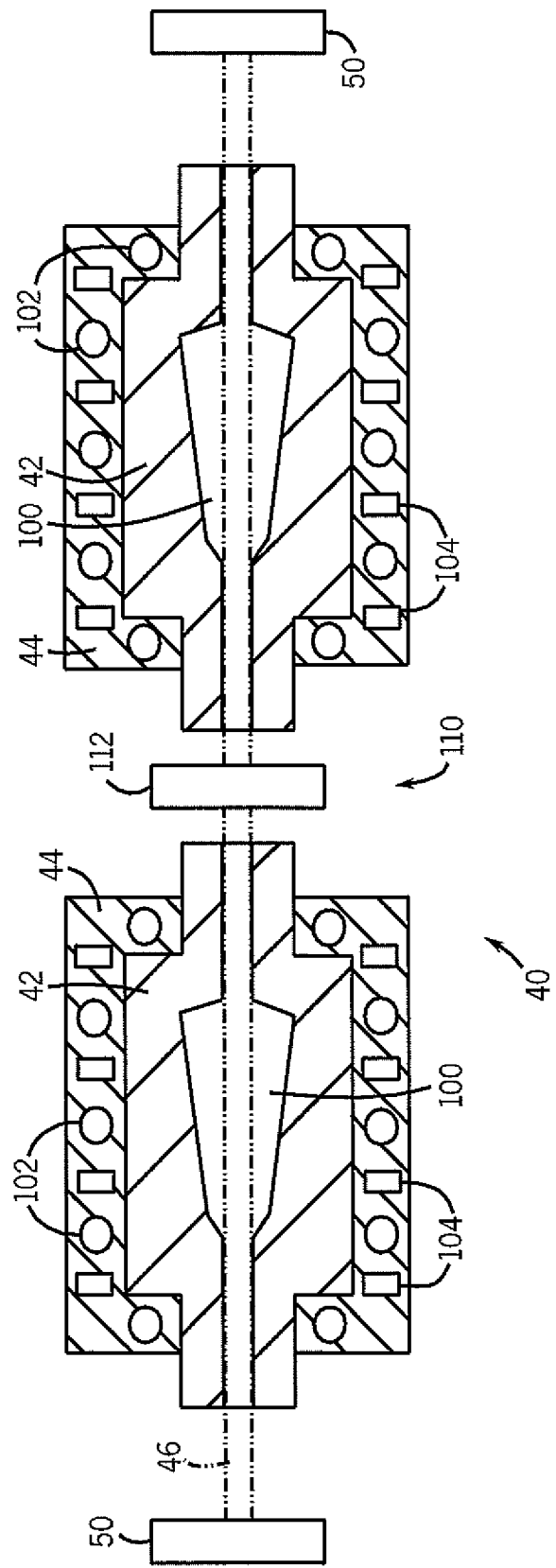
FIG. 9 depicts an additional embodiment of molds arranged in series with an additional clamp disposed between the molds, in accordance with aspects of the present disclosure.

Turning to FIG. 9, in a further embodiment, an additional clamp 112 may be provided between the molds 42. The additional clamp 112 may prevent the flow of nitrogen or other gas between the molds 42. For example, in one embodiment each clamp 50 may be associated with a respective nozzle (as opposed to a single nozzle being employed to blow gas into the tube 46). Additional clamp 112 and the respective nozzle associated with each clamp 50 may allow a different pressure profile to be employed with each mold 42 (e.g., one mold 42 may be pressurized to a different pressure and/or for a different interval than the other). Such pressure independence may be desirable in certain implementations.

Figure 10:
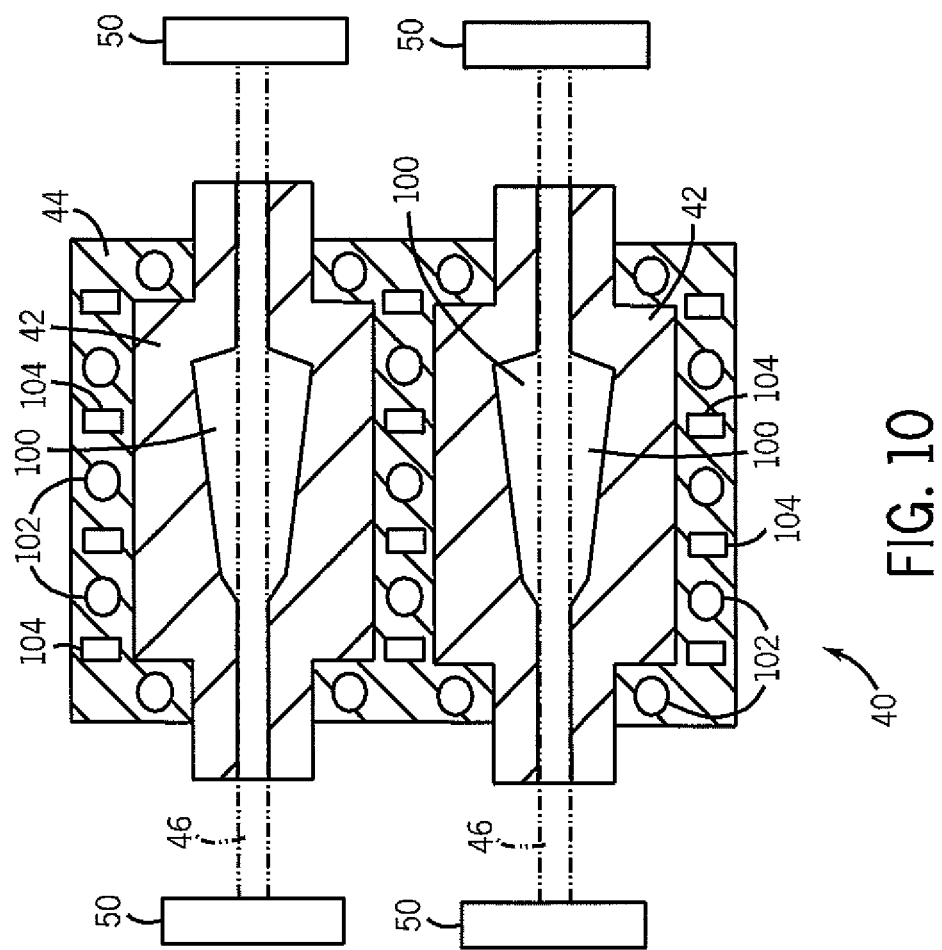
FIG. 10 depicts an embodiment of cuff molds arranged in parallel in accordance with aspects of the present disclosure.

Turning to FIG. 10, a parallel arrangement of molds 42 in a common or shared heating/cooling jacket 44 is depicted. In such an arrangement, each mold 42 may be loaded with a different respective tube 46. Likewise, different respective sets of clamps 50, i.e., one set for each tube 46, may be employed. In this manner, in one embodiment the different respective tubes 46 may be subjected to different amount of tension and/or the duration of the tension may be different for each tube 46. In such an embodiment, the blow molding machine 38 may be provided with separate servo motors to control movement of the respective clamps 50 so that the respective tubes 42 may be stretched independent of one another.

Figure 11:
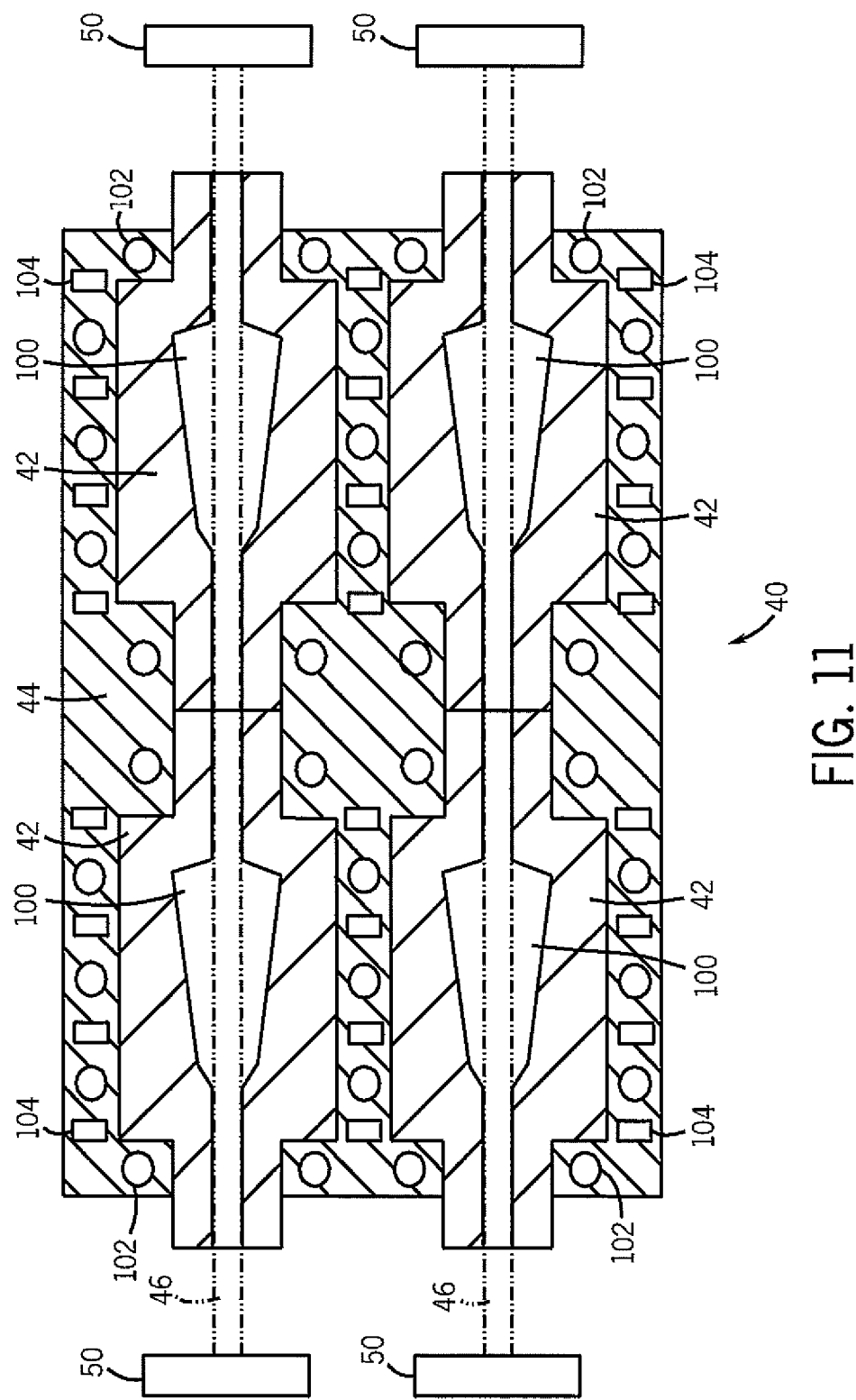
FIG. 11 depicts an embodiment of cuff molds arranged in series and in parallel in accordance with aspects of the present disclosure.

Turning to FIG. 11, a combination parallel and serial arrangement of molds 42 is depicted. In this arrangement, two pairs of serially arranged molds are provided in parallel, allowing production of four cuffs (two cuffs in each tube 46) for each blow molding operation. In the depicted embodiment, the molds 42 are loaded into a common or shared heating cooling jacket 44, though in other embodiments each mold 42, each serial combination of molds, and/or each parallel combination of molds may be loaded into separate respective heating/cooling jackets 44. Likewise, in the depicted embodiment, the serially arranged molds 42 are in contact with one another. In other embodiments, the serially arranged molds 42 may be spaced apart to reduce or eliminate heat transfer between molds 42.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to forming cuffs for tracheal tubes but for any type of device designed for insertion into a human or animal body for which a tight seal is desired.

What is claimed is:

1. A tube, comprising:
   a forming tube comprising a tube wall; and
   two or more cuffs formed from respective blown out portions of the tube wall, wherein the two or more cuffs are mirror images of each other and are configured to be separated from one another and to be incorporated onto respective endotracheal tubes as an endotracheal tube cuff.

2. The tube of claim 1, wherein the forming tube is about 12 inches (30.48 cm) in length.

3. The tube of claim 1, wherein the forming tube comprises a polymeric composition.

4. The tube of claim 3, wherein the polymeric composition comprises polyurethane.

5. The tube of claim 1, wherein the forming tube has an inner diameter between about 0.1708 inches and 0.296 inches (4.34 mm to 7.52 mm).

6. The tube of claim 1 wherein each cuff comprises wall that are 0.00086 inches (0.022 mm) thick or less.

7. The tube of claim 1, wherein each cuff is tapered.

8. A blow molding system, comprising:
   two or more molds, each comprising a cavity corresponding to a shape of a cuff, wherein the two or more molds are mirror images of each other, and wherein each cuff is configured to be separated from a forming tube and attached to a respective endotracheal tube body to form an endotracheal tube;
   one or more heating/cooling jackets configured to secure the two or more molds and to actively heat and cool the two or more molds; and
   two or more clamps, wherein the one or more heating/cooling jackets and the two or more molds are positioned between at least two of the clamps that are configured to move toward and away from the one or more heating/cooling jackets and the two or more molds.

9. The blow molding system of claim 8, comprising a control station configured to control operation of the one or more heating/cooling jackets and the two or more clamps.

10. The blow molding system of claim 8, wherein each mold is secured in a respective heating/cooling jacket.

11. The blow molding system of claim 8, wherein at least two molds are secured in each heating/cooling jacket.

12. The blow molding system of claim 8, wherein the two or more molds are arranged in series.

13. The blow molding system of claim 8, wherein the two or more molds are arranged in parallel.

14. A mold assembly, comprising:
   two or more molds, each comprising a cavity corresponding to a shape of a cuff, wherein the two or more molds are minor images of each other, and wherein each cuff is configured to be separated from a forming tube and attached to a respective endotracheal tube body to form an endotracheal tube; and
   one or more heating/cooling jackets configured to secure the two or more molds and to actively heat and cool the two or more molds.

15. The mold assembly of claim 14, wherein the two or more molds comprise beryllium copper.

16. The mold assembly of claim 14, wherein the two or more molds are arranged in series in a heating/cooling jacket or in separate respective heating/cooling jackets.

17. The mold assembly of claim 14, wherein the two or more molds are arranged in parallel in a heating/cooling jacket or in separate respective heating/cooling jackets.

18. The mold assembly of claim 14, wherein four or more molds are arranged in series and in parallel in the one or more heating/cooling jackets such that a first subset of the molds are situated end-to-end with respect to one another but side-by-side with respect to a second subset of the molds.

19. A method of manufacturing two or more inflatable cuffs in a single operation comprising:
   clamping each end of a forming tube, wherein portions of the forming tube are positioned within two or more molds, wherein the two or more molds are minor images of each other;
   stretching the forming tube by pulling the ends of the forming tube away from the two or more molds;

increasing the pressure within the forming tube such that the portions of the forming tube within the two or more molds are blown outward to conform to the shape of the molds to form two or more cuffs, wherein each cuff is configured to be separated from the forming tube and attached to a respective endotracheal tube body to form an endotracheal tube;

heating the molds for an interval of time;

cooling the molds;

decreasing the pressure within the tube;

removing tension on the tube by moving the ends of the tube toward the two or more molds; and releasing the ends of the tube.

20. A method of manufacturing two or more inflatable cuffs in a single operation comprising:

loading one or more tubes into a mold assembly comprising two or more molds, wherein the two or more molds are mirror images of each other;

initiating a blow molding program on a blow molding machine, wherein the blow molding program initiates and controls stretching, heating, pressurizing, and cooling operations performed by the blow molding machine such that a cuff is formed in a respective portion of tube disposed within each of the two or more molds;

removing the one or more tubes from the mold assembly, wherein each tube comprises at least two cuff regions; and cutting the cuff regions from the one or more tubes to form two or more cuffs.

21. The method of claim 20, comprising attaching each of the two or more cuffs to a respective endotracheal tube body to form respective endotracheal tubes.

22. A mold assembly, comprising:

two molds, each comprising a cavity corresponding to a shape of a cuff having a distal end and a proximal end, and wherein the two molds are arranged end to end such that the distal end of one cavity is adjacent to the proximal end of the other cavity, and wherein each cuff is configured to be separated from a forming tube and attached to a respective endotracheal tube body to form an endotracheal tube; and one or more heating/cooling jackets configured to secure the two molds and to actively heat and cool the two molds.

23. The mold assembly of claim 22, wherein each cavity is tapered.

* * * * *